(12) United States Patent
Xuenong et al.

(10) Patent No.: US 8,895,046 B2
(45) Date of Patent: Nov. 25, 2014

(54) ORTHOPAEDIC IMPLANT FOR SUPPORTING TISSUE GROWTH AND METHODS OF FORMING THE IMPLANT AND TISSUE

(75) Inventors: Zou Xuenong, Aarhus N. (DK); Haisheng Li, Viby J. (DK); Cody Bunger, Auning (DK)

(73) Assignee: Zimmer, Inc., Warsaw, IN (US)

( * ) Notice: Subject to any disclaimer, the term of this patent is extended or adjusted under 35 U.S.C. 154(b) by 1792 days.

(21) Appl. No.: 11/869,361

(22) Filed: Oct. 9, 2007

(65) Prior Publication Data

US 2008/0033548 A1 Feb. 7, 2008

Related U.S. Application Data

(63) Continuation of application No. 11/045,620, filed on Jan. 27, 2005, now abandoned.

(60) Provisional application No. 60/539,661, filed on Jan. 27, 2004.

(51) Int. Cl.

| | | |
|---|---|---|
| A61F 2/02 | (2006.01) | |
| A61F 2/28 | (2006.01) | |
| A61F 2/30 | (2006.01) | |
| A61F 2/32 | (2006.01) | |
| A61F 2/34 | (2006.01) | |
| A61F 2/36 | (2006.01) | |
| A61F 2/38 | (2006.01) | |
| A61F 2/44 | (2006.01) | |
| C12N 11/14 | (2006.01) | |
| C12N 11/02 | (2006.01) | |
| C12N 11/08 | (2006.01) | |
| C12N 5/07 | (2010.01) | |
| A61L 27/36 | (2006.01) | |
| A61L 27/38 | (2006.01) | |
| A61F 2/46 | (2006.01) | |
| A61F 2/00 | (2006.01) | |

(52) U.S. Cl.
CPC ........... *A61L 27/3608* (2013.01); *A61F 2/4644* (2013.01); *A61F 2310/00976* (2013.01); *A61F 2310/00341* (2013.01); *A61F 2002/2867* (2013.01); *A61F 2/32* (2013.01); *A61F 2002/30199* (2013.01); *A61F 2/44* (2013.01); *A61F 2310/00491* (2013.01); *A61F 2002/3093* (2013.01); *A61F 2002/2817* (2013.01); *A61F 2230/0063* (2013.01); *A61F 2/3094* (2013.01); *A61F 2002/30981* (2013.01); *A61F 2002/30678* (2013.01); *A61F 2310/00982* (2013.01); *A61F 2230/0069* (2013.01); *A61L 27/38* (2013.01); *A61F 2002/30677* (2013.01); *A61F 2002/30225* (2013.01); *A61F 2/30767* (2013.01); *A61F 2/34* (2013.01); *A61F 2002/0086* (2013.01); *A61F 2/28* (2013.01); *A61F 2310/00544* (2013.01); *A61F 2310/00293* (2013.01); *A61F 2002/4648* (2013.01); *A61F 2/38* (2013.01); *A61F 2310/00161* (2013.01); *A61F 2/36* (2013.01)
USPC .......... 424/423; 424/93.7; 435/176; 435/177; 435/180; 435/395; 435/402

(58) Field of Classification Search
None
See application file for complete search history.

(56) References Cited

U.S. PATENT DOCUMENTS

| | | | |
|---|---|---|---|
| 4,487,808 A | | 12/1984 | Lambert |
| 5,160,490 A | * | 11/1992 | Naughton et al. ......... 435/287.1 |
| 5,278,063 A | * | 1/1994 | Hubbell et al. ............... 435/402 |
| 5,282,861 A | | 2/1994 | Kaplan |
| 5,409,703 A | | 4/1995 | McAnalley et al. |
| 5,443,519 A | * | 8/1995 | Averill et al. ............... 623/22.22 |
| 5,464,440 A | | 11/1995 | Johansson |
| 5,509,899 A | | 4/1996 | Fan et al. |
| 5,612,052 A | | 3/1997 | Shalaby |
| 5,702,487 A | * | 12/1997 | Averill et al. ............... 623/23.35 |
| 5,714,159 A | | 2/1998 | Shalaby |
| 6,080,488 A | | 6/2000 | Hostettler et al. |
| 6,110,483 A | | 8/2000 | Whitbourne et al. |
| 6,176,849 B1 | | 1/2001 | Yang et al. |
| 6,179,872 B1 | * | 1/2001 | Bell et al. ................... 623/11.11 |
| 6,410,044 B1 | | 6/2002 | Chudzik et al. |
| 6,413,539 B1 | | 7/2002 | Shalaby |
| 6,544,472 B1 | | 4/2003 | Compton |
| 6,793,675 B2 | * | 9/2004 | Shapiro et al. ............. 623/11.11 |
| 6,916,640 B2 | * | 7/2005 | Yu et al. ......................... 435/182 |
| 7,192,769 B2 | * | 3/2007 | Pykett et al. .................. 435/373 |
| 2003/0036794 A1 | | 2/2003 | Ragheb et al. |

OTHER PUBLICATIONS

Bobyn JD, Stackpool GJ, Kacking SA, Tanzer M. Krygier JJ. Characteristics of bone ingrowth and interface mechanics of a new porous tantalum biomaterial. J. Bone Joint Surg Br. 1999;81:907-14.

Bobyn JD, Toh KK. Hacking SA, Tanzer M., Krygier JJ. Tissue response to porous tantalum acetabular cups: a canine model. J. Arthroplasty. 1999; 14:347-54.

(Continued)

*Primary Examiner* — David M Naff
(74) *Attorney, Agent, or Firm* — Schwegman Lundberg & Woessner, P.A.

(57) ABSTRACT

Adult autologous stem cells cultured on a porous, three-dimensional tissue scaffold-implant for bone regeneration by the use of a hyaluronan and/or dexamethasone to accelerate bone healing alone or in combination with recombinant growth factors or transfected osteogenic genes. The scaffold-implant may be machined into a custom-shaped three-dimensional cell culture system for support of cell growth, reservoir for peptides, recombinant growth factors, cytokines and antineoplastic drugs in the presence of a hyaluronan and/or dexamethasone alone or in combination with growth factors or transfected osteogenic genes, to be assembled ex vivo in a tissue incubator for implantation into bone tissue.

33 Claims, 4 Drawing Sheets

(56) References Cited

OTHER PUBLICATIONS

Zou X, Li H. Bunger M. Egund N. Lind M. Bunger C. Bone ingrowth characteristics on the porous tantalum and carbon fiber interbody fusion devices: an experimental study in pigs. Presented at the 2002 ISSLS annual meeting, Cleveland, 2002 and the 49th Annual Meeting of ORS, New Orleans, 2003.

Zou X, Xue Q, Li H. Bunger M. Lind M. Bunger C. Effect of alendronate on bone ingrowth into porous tantalum and carbon fiber interbody devices: an experimental study in pigs. Acta Orthopaedica Scandinavica 2003 (in press).

Zou X, Li H, Teng X, Egund N, Lind M, Bunger C. Pedicle screw fixation and a porous tantalum interbody device results in natural bony appearance: an experimental study in pigs. (unpublished).

Bagley J, Rosenzweig M, Marks DF, Pykett NJ. Extended culture of multipotent hematopoietic progenitors without cytokine augmentation in a novel three-dimensional device. Exp. Hematol. 1999; 27:496-504.

Rosenzweig M, Pykett M, Marks DF, Johnson R. Enhanced maintenance and retroviral transduction of primitive hematopoietic progenitor cells using a novel three-dimensional culture system. Gene Ther. 1997;4:928-36.

Maniatopoulos C, Sodek J. Melcher AH. Bone formation in vitro by stromal cells obtained from bone marrow of young adult rats. Cell Tissue Res. 1988;254:317-30.

Ohgushsi H, Dohi Y, Yoshikawa T, Tamai S, Tabata S, Okunaga K, et al. Osteogeneic differentiation of cultured marrow stromal stem cells on the surface of bioactive glass ceramics. J. Biomed Mater Res. 1996;32:341-1.

Yoshikawa T, Ohgushi H, Dohi Y, Davies JE. Viable bone formation in porous hydroxyapatite: marrow cell-derived in vitro bone on the surface of ceramics. Biomed Mater Eng. 1997;7:49-58.

Zou X, Li H, Baatrup A, Bunger C, and Lind M. Stimulation of procine bone marrow stromal cells by hyaluronan, dexamethasone, rhBMP-2. Presented at the 29th annual meeting of society for biomaterial, RENO, 2003.

Yoshikawa T, Ohgushi H, Akahane M, Tamai S, Ichijima K. Analysis of gene expression in osteogenic cultured marrow/hydroxyapatite construct implanted at ectopic sites: a comparison with the osteogenice ability of cancellous bone. J. Biomed Mater Res. 1998;41:568-73.

Bruder SP, Kraus KH, Goldberg VM, Kadiyala S. The effects of implants loaded with autologous mesenchymal stem cells on the healing of canine segmental bone defects. J. Bone Joint Surg. Am 1998;80:985-96.

Yoshikawa T, Ohgushi H, Uemura T, Nakajima H, Ichijima K, Tamai S, Tateisi T. Human marrow cells derived cultured bone in porous ceramics. Biomed Mater Eng. 1998;8:311-20.

Yoshikawa T, Ohgushi H, Tamai S. Immediate bone forming capability of prefabricated osteogenic hydroxyapatite. J Biomed Mater Res. 1996;32:481-92.

Xuenong Zou, Haishen Li, Anette Baatrup, Martin Lind, Cody Bunger. Engineering of Bone Tissue with Porcine Bone Marrow Stem Cells in Three-Dimensional Trabecular Metal: In vitro and in vivo studies. APMIS Suppl. 109, vol. 111, 127-132, 2003.

* cited by examiner

ORTHOPAEDIC IMPLANT FOR SUPPORTING TISSUE GROWTH AND METHODS OF FORMING THE IMPLANT AND TISSUE

RELATED APPLICATIONS

This application is a Continuation of U.S. patent application Ser. No. 11/045,620 filed Jan. 27, 2005, now abandoned, which is based on U.S. Provisional Patent Application Ser. No. 60/539,661 filed Jan. 27, 2004, the disclosures of which are hereby explicitly incorporated by reference herein.

FIELD

The invention relates to tissue generation. More particularly, the invention relates to three-dimensional tissue generation by ex vivo three-dimensional cell culture methods using porous, three-dimensional tissue scaffold-implants.

BACKGROUND

The current trend of tissue engineering technology is toward the development of biomaterials for repairing tissue defects or to enhance fixation of implants to the host tissue. Basic requirements include a scaffold-implant conductive to cell attachment and maintenance of cell function, together with a rich source of progenitor cells. Biomaterials in combination with cells from ex-vivo cultures will not only accelerate the tissue healing, but also increase the biocompatibility of scaffold-implants to shorten the hospitalization, and improved long-term function of the devices. In particular, patients with large defects, impaired bone healing and cancer disease in the region of repair shall benefit from this new technology. One regenerative tissue engineering approach involves a process known as "tissue induction", whereby a two or three-dimensional polymer or mineral scaffold-implant without cells is implanted into a patient. With tissue induction, tissue generation occurs through ingrowth of surrounding tissue into the scaffold-implant.

Another approach to tissue generation, known as "cell transplantation", involves seeding a scaffold-implant with cells, cytokines, and other growth-related molecules, then culturing and implanting the scaffold-implant into the subject to induce the growth of new tissue. Cultured cells are infused in a biodegradable or non-biodegradable scaffold-implant, which may be placed in a bioreactor in-vitro to allow the cells to proliferate before the cells containing scaffold-implant is implanted in the patient. Alternatively, the cell-seeded scaffold-implant may be directly implanted, in which case the patient's body acts as an in-vivo bioreactor. Once implanted, in-vivo cellular proliferation and, in the case of absorbable scaffold-implants, concomitant bio-absorption of the scaffold-implant, proceeds.

In both types of tissue engineering, i.e., tissue induction and cell transplantation, the scaffold-implant, whether or not bio-absorbable, must be biocompatible, such that it does not invoke an adverse immune response from, or result in toxicity to, the patient.

Several types of materials have been investigated for use as seeding scaffold-implants, including metals, ceramics, polymers, and polymer-coated metals and ceramics. Existing scaffold-implants may be manufactured by solvent casting, shaping sections with machining, 3D printing, or molded collagen/cell constructs. While the aforementioned scaffold-implant materials are primarily for industrial applications, the fabrication of hydroxyapatite scaffold-implants using selective laser sintering and polymer-coated calcium phosphate powder, have been investigated. Additional post-processing, such as high temperature heating which burns out the binder, and then higher temperature sintering which fuses the powder together, is required to strengthen the scaffold-implant.

Whichever type of scaffold-implant is selected, a purpose of the scaffold-implant is to support cells, which, after being seeded into the device, cling to the interstices of the scaffold-implant, replicate, produce their own extra-cellular matrices, and organize into the target tissue. For example, in the case of bone regeneration, the optimal pore size for maximum tissue growth ranges from 200-400 microns ($\mu m$). Therefore, the material or materials used for fabricating the scaffold-implant should have this pore size (200-400 $\mu m$) and have sufficient rigidity and biomechanical properties to support loads that are used for generating bone tissue.

Scaffold-implants fabricated from a material such as hydroxyapatite, which is useful for supporting bone cells, are too brittle and non-pliable to act as scaffolding for muscle or tendons. Many of the polymers, and the polymer-coated metals and ceramics present a challenge to seeding cells in three-dimensional scaffolds. None of the known scaffold-implant materials allow growth of cells to a depth of greater than about 250 $\mu m$, which is a generally accepted practical limit on the depth to which cells and nutrients can diffuse into scaffold-implants having the desired porosities. Even if cells could be made to diffuse to greater depths, it is generally believed that to support cell growth and avoid or at least curtail apoptosis at these depths, the scaffold-implant must also support some form of vasculature to promote angiogenesis; none of the earlier mentioned scaffold-implant fabrication methods, however, allow for incorporation of blood vessels.

Porous, three-dimensional metallic structures have recently been developed for potential application in reconstructive orthopaedics and other surgical disciplines. Such structures are described in U.S. Pat. No. 5,282,861 entitled "Open Cell Tantalum Structures For Cancellous Bone Implants And Cell And Tissue Receptors" issued to Kaplan; U.S. Pat. No. 5,443,515 entitled "Vertebral Body Prosthetic Implant With Slidably Positionable Stabilizing Member" issued to Cohen et al.; U.S. Pat. No. 5,755,809 entitled "Femoral Head Core Channel Filling Prosthesis" issued to Cohen et al.; U.S. Pat. No. 6,063,442 entitled "Bonding Of Porous Materials To Other Materials Utilizing Chemical Vapor Deposition" issued to Cohen et al.; and U.S. Pat. No. 6,087,553 entitled "Implantable Metallic Open-Celled Lattice/Polyethylene Composite Material And Devices" issued to Cohen et al., the disclosures of which are incorporated herein by reference. The porous, three-dimensional metallic structure is a bio-compatible material having a three-dimensional network of continuously interconnected channels or pores which define a three-dimensional porosity, i.e., volume porosity, ranging from 50 to 90% (higher than all other known implant materials). This high bulk volume porosity readily facilitates nutrient diffusion and media circulation.

The porous, three-dimensional metallic structures may be fabricated using a vapor deposition/infiltration process wherein tantalum, which has a long history of medical uses, or other bio-compatible metal or material is vaporized at high temperature and precipitated as a thin layer onto a carbon lattice. The coating of tantalum or other metal enhances or improves the strength or mechanical characteristics of the carbon lattice.

As a scaffold for "bone induction," preliminary animal studies with transcortical (bone conduction) porous, three-dimensional metallic structures have been shown to support rapid and extensive bone ingrowth. For example, tissue response to porous tantalum acetabular cups indicates that the porous tantalum material is effective for biologic fixation. The biomechanical property of the porous tantalum biomaterial is sufficient to withstand physiological load for specific applications, such as an acetabular cup, a spinal fusion, and a vertebral body replacement in fractures or in metastatic cancer disease. As a scaffold for "cell transplantation," porous, three-dimensional metallic structures can extend culturing of multipotent hematopoietic progenitors without cytokine augmentation and enhance maintenance and retroviral transduction of primitive hematopoietic progenitor cells.

Hyaluronan possesses biochemical and physical properties suitable to perform an important role in the early events of osteogenesis as well as in many other tissues. A low-molecular weight hyaluronan fully expresses the in-vitro osteogenic potential of mesenchymal cells through the subsequent proliferation and differentiation of osteoprogenitor cells using proper conditions. Locally applied high-molecular hyaluronan of MW 1900 kDa also has been shown to be capable of accelerating new bone formation through mesenchymal cell differentiation in femur wounds. Hyaluronan at a low concentration (0.5 mg/mL) has been shown to increase the development of porcine embryos in culture.

SUMMARY

One aspect is a three-dimensional tissue scaffold-implant for supporting tissue (e.g., bone) on-growth. The tissue scaffold-implant comprises a lattice having a matrix of interconnected pores which form surfaces in three dimensions; and an inert, biocompatible material covering the surfaces. The surfaces of the scaffold-implant define a high surface area relative to a volume of the scaffold-implant.

Another aspect is a method of forming tissue (e.g., bone). The method comprises providing a three-dimensional tissue scaffold comprising a lattice having a matrix of interconnected pores which form surfaces in three dimensions, and an inert, biocompatible material covering the surfaces; covering the biocompatible material covered surfaces of the scaffold with cells; and culturing the scaffold to grow tissue on and in the scaffold.

Yet another aspect is a method of making an implant for supporting tissue (e.g., bone) on-growth. This method comprises providing a three-dimensional tissue scaffold comprising a lattice having a matrix of interconnected pores which form surfaces in three dimensions, and an inert, biocompatible material covering the surfaces; and covering the biocompatible material covered surfaces of the scaffold with cells.

DETAILED DESCRIPTION

The tissue formation method of the present invention utilizes an ex vivo cell culture system and a porous, three-dimensional metallic structure or tissue scaffold of a desired shape and size, which will be implanted into the body of an animal or human being (hereinafter scaffold-implant). The cell culture system induces early stage cell proliferation and differentiation on and in the tissue scaffold-implant, resulting in tissue generation. The tissue formation method of the present invention is especially useful for generating bone tissue. The method of the invention may also be used to generate connective tissue and hematopoietic tissue.

Figure 1:
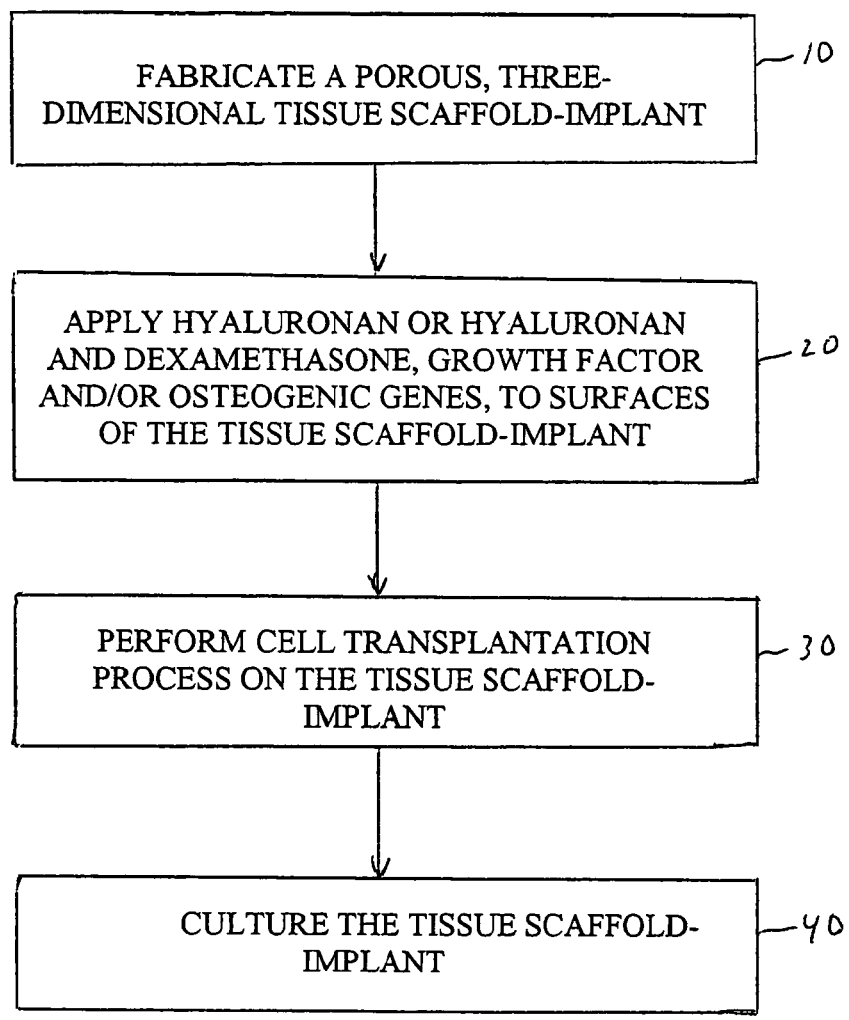
FIG. 1 is a flow chart depicting an embodiment of the method of the present invention.

The flow chart of FIG. 1 depicts an embodiment of the tissue formation method of the present invention. In step 10 of the method, a porous, three-dimensional tissue scaffold-implant is fabricated in a desired shape and size, e.g., hip implant, spinal implant, knee implant, etc. For example, the scaffold-implant may be shaped and sized as a prosthetic acetabular cup such as the one disclosed in U.S. Pat. No. 5,443,519 entitled "Prosthetic Ellipsoidal Acetabular Cup," issued to Averill et al. In another example, the scaffold-implant may be shaped and sized as a prosthetic femoral component such as the one disclosed in U.S. Pat. No. 5,702,487 entitled "Prosthetic Device" issued to Averill et al.

In one embodiment, the scaffold-implant may be fabricated as a single unitary member. In an alternative embodiment, the scaffold-implant may be fabricated as a single, integral member formed by two or more separately fabricated sections which are mechanically assembled together in a conventional manner. In still another embodiment, the scaffold-implant may be fabricated as an assembly of two or more cooperating, unitary and/or integral members (e.g., acetabular cup and femoral stem/ball assembly).

The porous, three-dimensional tissue scaffold-implant may comprise a carbon lattice having a strut or ligament skeleton which forms a three-dimensional network of continuously interconnected channels or pores each roughly approximating a dodecahedron, which create a series of continuous microniches and form surfaces of the lattice in three dimensions; and a thin film of an inert, bio-compatible metal or other bio-compatible material, which covers the surfaces.

The carbon lattice may be formed as a single, unitary member of a desired shape and size, or in sections of desired shapes and sizes to be mechanically assembled. The carbon lattice is substantially rigid, therefore, it may be machined into a bone regeneration tool of a desired shape and size using conventional machining methods.

The inert, bio-compatible metal or other bio-compatible material may be applied to the surfaces of the carbon lattice using conventional vapor depositing and infiltrating methods. In a preferred embodiment, the inert, biocompatible metal comprises tantalum. In other embodiments, the inert, biocompatible metal may comprise niobium or alloys of tantalum and niobium.

The completed porous, three-dimensional tissue scaffold-implant forms a three-dimensional network of continuously interconnected, channels or pores which define a three-dimensional porosity (volume porosity). In one embodiment, the tissue scaffold implant may comprise channels or pores having an average diameter of 400 to 500 µm and a volume porosity ranging from about 50 to about 90%. The geometry of the interconnected pores and surface texturing arising from the metal vapor deposition process produce high surface area-to-volume ratio. The large pores and surfaces allow attachment of proteins, peptides and differentiated and undifferentiated cells. After fabrication, the scaffold-implant may be coated with substrate molecules such as fibronectin and collagens which aid in the attachment of the proteins, peptides and differentiated and undifferentiated cells.

In step 20, a hyaluronan (also referred to as hyaluronic acid or sodium hyaluronate) or a hyaluronan, dexamethasone, one or more growth factors and/or osteogenic genes is (are) applied to the surfaces of the tissue scaffold-implant to stimulate early cell proliferation and differentiation, therefore accelerating tissue generation. Sodium hyaluronate is a natural high-viscosity anionic mucopolysaccharide with alternating beta (1-3) glucuronide and beta (1-4) glucosaminidic bonds. It is commonly found in the umbilical cord, in vitreous humor, in synovial fluid, in pathologic joints, in group A and C hemolytic streptococci, and in Wharton's jelly. Dexamethasone is a synthetic steroid compound. In one embodiment, the tissue scaffold-implant may be treated with a low concentration (4 mg/mL) of sodium hyaluronate to induce in-vitro, early stage stem cell proliferation and differentiation on and in the tissue scaffold-implant (after performing steps 30 and 40 to be described further on). In another embodiment, the tissue scaffold-implant may be treated with a high concentration (10-20 mg/mL) of sodium hyaluronate which forms a hydro gel with the stem cells in the tissue scaffold-implant intraoperatively.

In step 30 of the method, a cell transplantation process is performed on the porous, three-dimensional tissue scaffold-implant. In an embodiment of the cell transplantation process, the tissue scaffold-implant is seeded with living cells, which may comprise differentiated, undifferentiated or gene transfected cells. Examples of differentiated or undifferentiated cells include without limitation bone marrow cells, osteoblasts, mesenchymal stem cells, embryonic stem cells, endothelial cells. In another embodiment of the cell transplantation process, the tissue scaffold-implant is seeded with living cells and proteins, peptides, transcript factors, osteogenic genes, cytokines, therapeutic agents, and growth factors.

The living cells and other factors can be entrapped and delivered in the tissue scaffold-implant by means of a versatile self-assembly method. In this self-assembly method cellular matrix fibrils are formed with methylated collagen (type I) and hyaluronic acid, or chitosan, which entrap and deliver living cells and other factors. The cellular matrix fibrils are then combined with an outer-layer membrane comprising a polymer such as alginate, hydroxylethyl methacrylate (HEMA), or a terpolymer of hydroxylethyl methacrylate (HEMA), methy methacrylate (MMA) and methylacric acid (MAA) by complex sandwich conjugation achieved, for example, using a complex coacervation process, to protect transplanted allogeneic cells from immune attacks and to sustain release of the stimulating factors and therapeutic agents. In one embodiment, the membrane may be several micrometers to about 100 micrometers thick. The thickness of the membrane may be adjusted by controlling the concentrations and contact time of polyelectrolytes in the complex sandwich conjugation process.

The surface features (the texture on the surface of the metal resulting from the CVD of the metal) and the open, highly interconnected pores of the tissue scaffold-implant readily facilitate nutrient diffusion and media circulation and thus will operate as conduits for cell infusion, adhesion, mass transfer, or to stimulate angiogenesis for blood flow.

In an alternate embodiment, the application of the hyaluronan or the hyaluronan, dexamethasone, one or more growth factors and/or osteogenic genes, to the surfaces of the tissue scaffold-implant (step 20) may be performed during the cell transplantation process of step 30.

In step 40, after seeding, the scaffold-implant is cultured in a bioreactor to generate the desired tissue. In one embodiment, the culturing step is an ex-vivo process. Ex-vivo culturing may be performed in a broth medium, e.g., Dulbecco's modified Eagle's medium (DMEM) available from HyClone, plus 10% fetal calf serum, which is placed in an incubator e.g., perfusion or spiner flask bioreactor or a rotating bioreactor. The broth medium and incubator operate as an in-vitro bioreactor. In one embodiment, the incubator may provide a humidified atmosphere of 95% air and 5% $CO_2$ at 37° C. In addition, the incubator may be of the type which provides static, dynamic medium flow, pulsatile air flow, microgravity and multidirectional gravity culturing conditions. The scaffold-implant may then be implanted (in-vivo) into an animal or patient's body.

In another embodiment, the culturing step is an in-vivo process. In-vivo culturing may be performed in an animal or a patient by directly implanting the scaffold-implant in the animal or the patient. In this embodiment, the animal or the patient' body operates as an in-vivo bioreactor.

In still an alternate embodiment, the culturing step can be performed intraoperatively. In this embodiment, cells are taken from the animal or patient and applied to the scaffold-implant. The scaffold-implant is then implanted in the animal or patient.

Figure 2:
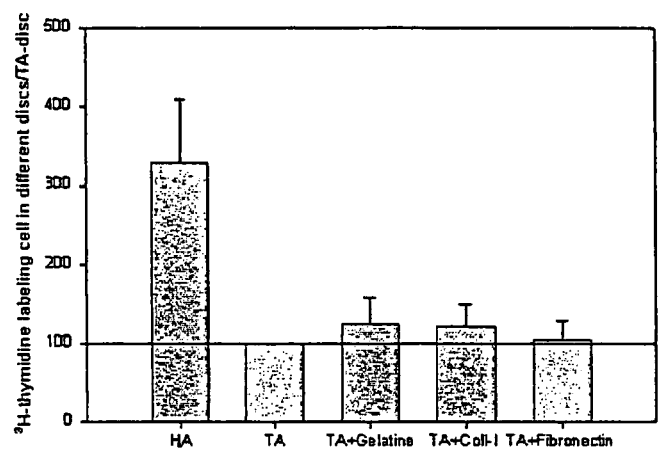
FIG. 2 is a bar graph quantifying stem cells binding to a coralline hydroxyapatite disc and uncoated and coated porous tantalum discs, after a 24-hour incubation at 37° C. and normalized to the uncoated TA disc.

FIG. 2 is a bar graph quantifying stem cells binding to 1) a coralline hydroxyapatite (HA) disc; 2) an uncoated porous, tantalum-based, three-dimensional tissue scaffold-implant (TA) configured as a disc; 3) a TA disc coated with gelatin; 4) a TA disc coated with type I collagen; and 5) a TA disc coated with fibronectin, n=9 (repeated test), after a 24-hour incubation at 37° C. and normalized to the uncoated TA disc. In the graph, the stem cells are $^3$H-thymidine labeling cells.

Figure 3A:
FIGS. 3A and 3B are Hoechst stained fluorescent micrographs at 50× original magnification and 20× original magnification respectively, showing the growing stem cells in the pores of porous tantalum after 7 days of incubation.
Figure 3B:

FIGS. 3A and 3B are fluorescent micrographs showing the growing cells in the pores of a porous, tantalum-based, three-dimensional tissue scaffold-implant configured as a disc after 7 days of incubation (Hoechst staining). As can be seen in FIG. 3A, at day 7, porcine bone marrow stem cells depicted funicular proliferations of spindle cells on the pore surface and within the pores. As shown in FIG. 3B, growing stem cells in the pores mainly distributed on the surface areas of disc (superior) where the cells were loaded on. Only a few stem cells had grown into the central pores and down to other surface areas of the disc (inferior) where the disc was seated on a well.

Figure 4A:
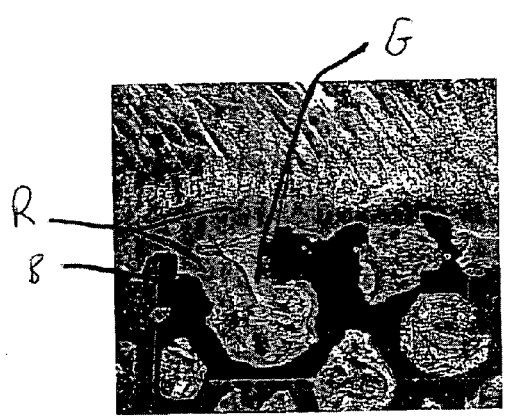
FIGS. 4A and 4B are histological micrographs at 20× original magnification and 6.25× original magnification respectively, after 8 weeks of implantation in pigs.
Figure 4B:
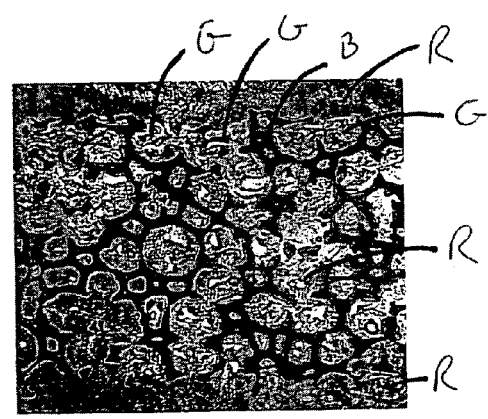

FIGS. 4A and 4B are histological micrographs which show, after 8 weeks of implantation in pigs, ectopic bone formation after autologous bone marrow stem cells cultured with a tantalum-based, three-dimensional tissue scaffold-implant for 7 days of incubation. Basic fuchsin and light green staining revealed the bone is green G and fibrous tissue is red R. The black structure B is porous tantalum strut. Specifically, FIG. 4A shows bone forming in the pore surface and the pores and FIG. 4B shows a layer of de novo bone formation at the surface area of the scaffold-implant.

Figure 5:
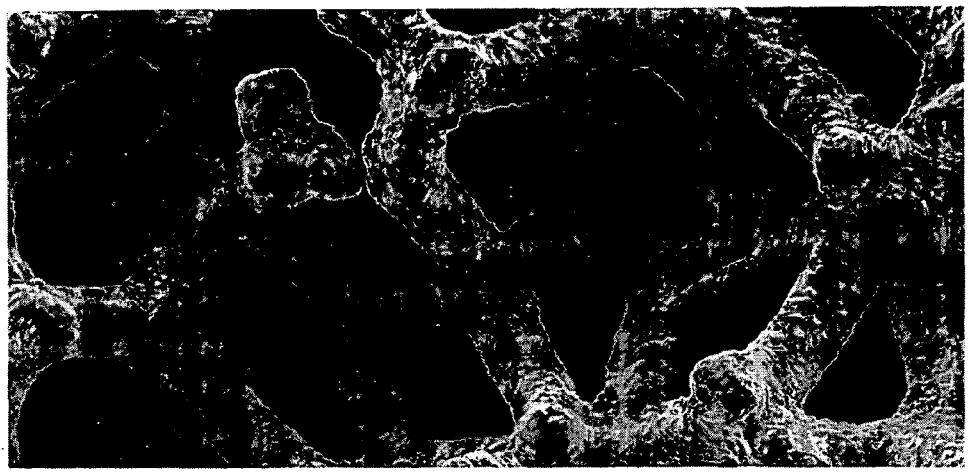
FIG. 5 is a scanning electronic micrograph of the three-dimensional tissue scaffold-implant.

FIG. 5 is a scanning electronic micrograph of the three-dimensional tissue scaffold-implant. As can be seen, the scaffold-implant has a volume porosity of about 50% to about 90% with interconnecting pores, allowing approximately 2-3 times greater bone ingrowth compared to conventional porous coatings.

Figure 6:
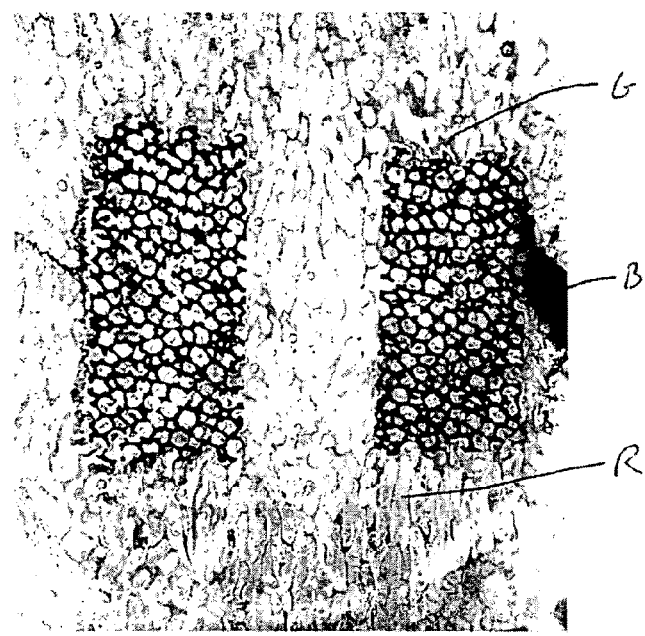
FIG. 6 is a histological micrograph of the three-dimensional tissue scaffold-implant after 12 weeks of implantation in a pig.

FIG. 6 is a histological micrograph of the three-dimensional tissue scaffold-implant after 12 weeks of implantation in a pig. As can be observed, there is bone formation from intraoperative conjugation of autologous bone marrow stem cells and hyaluronic acid gel in the tissue scaffold-implant. Basic fuchsin and light green staining revealed the bone is green G and fibrous tissue is red R. The black structure B is porous tantalum strut.

While the foregoing invention has been described with reference to the above, various modifications and changes can be made without departing from the spirit of the invention. Accordingly, all such modifications and changes are considered to be within the scope of the appended claims.

What is claimed is:

1. An orthopaedic three-dimensional tissue scaffold-implant for supporting tissue growth, the orthopaedic three-dimensional tissue scaffold-implant comprising:
   an inert, biocompatible material;
   a lattice forming a plurality of interconnected pores and including surfaces in three dimensions, the inert, biocompatible material applied to the surfaces of the lattice;
   at least one substance selected from the group consisting of a hyaluronan, dexamethasone, protein, peptide, transcript factor, cytokine, therapeutic agent, chitosan, polymer, osteogenic gene and growth factor applied to the inert, biocompatible material applied to the surfaces of the lattice; and
   living cells applied to the inert, biocompatible material applied to the surfaces of the lattice;
   wherein the lattice is a machined lattice machined to have a desired shape and size for subsequent implantation in a patient.

2. The tissue scaffold-implant of claim 1, wherein the inert, biocompatible material comprises a metal.

3. The tissue scaffold-implant of claim 2, wherein the metal comprises tantalum.

4. The tissue scaffold-implant of claim 1, wherein the inert, biocompatible material comprises a metal alloy.

5. The tissue scaffold-implant of claim 1, wherein the living cells are selected from the group consisting of bone marrow cells, osteoblasts, mesenchymal stem cells, embryonic stem cells, gene transfected cells, endothelial cells and combinations thereof.

6. The orthopaedic tissue scaffold-implant of claim 1 in the form of a hip implant, a spinal implant, or a knee implant.

7. The orthopaedic tissue scaffold-implant of claim 1 in the form of at least one of an acetabular cup and a femoral component.

8. A method of forming tissue, the method comprising:
   providing a three-dimensional tissue scaffold comprising a lattice and an inert, biocompatible material, the lattice forming a plurality of interconnected pores and including surfaces in three dimensions, the inert, biocompatible material applied to the surfaces of the lattice;
   machining the scaffold into an orthopaedic prosthesis having a desired shape and size;
   applying living cells to the biocompatible material of the scaffold; and
   culturing the living cells to grow bone tissue on and in the scaffold.

9. The method of claim 8, wherein prior to the culturing step, further comprising the step of applying at least one substance selected from the group consisting of a hyaluronan, dexamethasone, protein, peptide, transcript factor, cytokine, therapeutic agent, chitosan, polymer, osteogenic gene and growth factor, to the scaffold.

10. The method of claim 9, further comprising the step of encapsulating the at least one substance before applying the at least one substance.

11. The method of claim 10, wherein the encapsulating step comprises forming an outer-layer membrane comprising a polymeric material.

12. The method of claim 11, wherein the culturing step is performed by placing the scaffold in a medium and incubating the medium and scaffold.

13. The method of claim 12, further comprising the step of implanting the scaffold in the body of one of an animal and a human being.

14. The method of claim 9, wherein the culturing step is performed by implanting the scaffold in the body of one of an animal and a human being.

15. The method of claim 10, wherein the culturing step is performed by implanting the scaffold in the body of one of an animal and a human being.

16. The method of claim 8, wherein the culturing step is performed by placing the scaffold in a medium and incubating the medium and scaffold.

17. The method of claim 16, further comprising the step of implanting the scaffold in a body of one of an animal and a human being.

18. The method of claim 8, wherein the culturing step is performed by implanting the scaffold in the body of one of an animal and a human being.

19. The method of claim 8, wherein the inert, biocompatible material comprises tantalum.

20. The method of claim 8, wherein the living cells are selected from the group consisting of bone marrow cells, osteoblasts, mesenchymal stem cells, embryonic stem cells, gene transfected cells, endothelial cells and combinations thereof.

21. The method of claim 8, wherein the orthopaedic prosthesis has the desired shape and size of a hip implant, a spinal implant, or a knee implant.

22. The method of claim 8, wherein the orthopaedic prosthesis has the desired shape and size of at least one of an acetabular cup and a femoral component.

23. A method of making an orthopaedic implant for supporting tissue growth, the method comprising:
   providing a three-dimensional tissue scaffold having a desired shape and size for subsequent implantation in a patient, the three-dimensional tissue scaffold comprising a machined lattice and an inert, biocompatible metal, the machined lattice forming a plurality of interconnected pores and including surfaces in three dimensions which are coated by the inert, biocompatible metal;
   applying living cells to the inert, biocompatible metal of the scaffold; and
   culturing the living cells to grow bone tissue on and in the scaffold.

24. The method of claim 23, further comprising the step of applying at least one substance selected from the group consisting of a hyaluronan, dexamethasone, protein, peptide, transcript factor, cytokine, therapeutic agent, chitosan, polymer, osteogenic gene and growth factor, to the scaffold.

25. The method of claim 24, further comprising the step of encapsulating the at least one substance before applying the at least one substance.

26. The method of claim 25, wherein the encapsulating step comprises forming an outer-layer membrane comprising a polymeric material.

27. The method of claim 23, wherein the culturing step is performed by placing the scaffold in a medium and incubating the medium and scaffold.

28. The method of claim 23, wherein the culturing step is performed by implanting the scaffold in the body of one of an animal and a human being.

29. The method of claim 23, wherein the inert, biocompatible metal comprises tantalum.

30. The method of claim 23, wherein the living cells are selected from the group consisting of bone marrow cells, osteoblasts, mesenchymal stem cells, embryonic stem cells, gene transfected cells, endothelial cells and combinations thereof.

31. The method of claim 30, wherein the living cells are encapsulated in at least one of a hyaluronan, collagen, and chitosan and in an outer-layer membrane comprising a polymeric material.

32. The method of claim 23, wherein the orthopaedic implant has the desired shape and size of a hip implant, a spinal implant, or a knee implant.

33. The method of claim 23, wherein the orthopaedic implant has the desired shape and size of at least one of an acetabular cup and a femoral component.

* * * * *